United States Patent [19]

Pizzolante

[11] Patent Number: 4,748,125

[45] Date of Patent: May 31, 1988

[54] DISPOSABLE ADHESIVE TEST TUBE RACK

[76] Inventor: John M. Pizzolante, 4 Todd Rd., Woburn, Mass. 01801

[21] Appl. No.: 911,373

[22] Filed: Sep. 25, 1986

[51] Int. Cl.$^4$ .......... C12M 1/00

[52] U.S. Cl. .......... 435/287; 428/343; 422/104; D24/32; 206/44 R; 206/460; 206/813

[58] Field of Search .......... 435/296, 287; 206/45.21, 45.2, 44 R, 569, 227, 231, 372, 379, 460, 813; D24/32, 31; 428/343; 248/451, 453, 459; 211/73, 74; 422/104

[56] References Cited

U.S. PATENT DOCUMENTS

| | | | |
|---|---|---|---|
| D. 210,720 | 4/1968 | Anthon | D16/1 |
| D. 220,040 | 3/1971 | Carver | D6/99 |
| D. 231,444 | 4/1974 | Seitz et al. | D6/99 |
| 2,115,449 | 4/1938 | Pradt | 206/813 X |
| 2,142,194 | 1/1939 | Karfiol | 206/460 X |
| 2,695,097 | 11/1954 | Easton | 206/45.21 |
| 2,758,723 | 8/1956 | Morris et al. | 211/73 |
| 2,979,210 | 4/1961 | Patterson | 211/74 |
| 3,062,380 | 11/1962 | Grela et al. | 211/73 |
| 3,261,119 | 7/1966 | King | 206/813 X |
| 3,375,934 | 4/1968 | Bates | 211/72 |
| 3,390,783 | 7/1968 | Quackenbush | 211/73 |
| 3,731,819 | 5/1973 | Sandhage | 211/74 |
| 3,751,172 | 8/1973 | Seitz et al. | 356/244 |
| 3,802,844 | 4/1974 | Sendra et al. | 23/259 |
| 4,050,579 | 9/1977 | Gorski et al. | 206/460 |
| 4,105,115 | 8/1978 | Horvath et al. | 206/370 |
| 4,300,692 | 11/1981 | Moreno | 211/87 |
| 4,407,958 | 10/1983 | DeGraff, Jr. | 435/287 |

FOREIGN PATENT DOCUMENTS

| | | | |
|---|---|---|---|
| 926698 | 4/1955 | Fed. Rep. of Germany | 206/813 |
| 2904328 | 8/1980 | Fed. Rep. of Germany | 206/460 |
| 721480 | 1/1955 | United Kingdom | 206/460 |

*Primary Examiner*—Randall L. Green

[57] ABSTRACT

A test tube rack having a test tube-supporting member connected to a base member and bearing an adhesive strip is disclosed.

5 Claims, 4 Drawing Sheets

DISPOSABLE ADHESIVE TEST TUBE RACK

FIELD OF THE INVENTION

This invention relates to test tube racks, and more particularly to an elegantly simple disposable test tube holder employing an adhesive strip.

BACKGROUND OF THE INVENTION

A wide variety of test tube racks are known. Existing test tube racks generally have holes, slots, or arrangements of pegs to hold the test tubes. Some are adjustable and others are disposable. Presently known racks generally suffer from one or more of the following deficiencies: they accept only certain sizes of test tubes; they are not easily stored; in use, they obstruct the view of the contents of tubes held in them; they do not hold test tubes positively; if broken, they are not easily repaired; and they are generally not considered as disposable items.

In view of these general and other particular disadvantages of existing test tube racks, it would be very desirable to have an inexpensive test tube rack which is easily made, conveniently stored, quickly and simply assembled, easy to use with a wide variety of test tube sizes, does not block the view of the contents of test tubes held on it, and is easily repaired and safely disposable.

SUMMARY OF THE INVENTION

These and other advantages are provided by the test tube rack of the invention, which has a base, a test tube-supporting member having an outwardly-facing surface and a rear surface, this supporting member being connected to and making an angle with the base, and at least one adhesive strip mounted horizontally on the outwardly facing surface of the test tube-supporting member, this adhesive strip having an outwardly-facing layer of adhesive material on it.

DESCRIPTION OF THE DRAWING

The invention will be better understood from a consideration of the following detailed description, taken in conjunction with the drawing in which.

DETAILED DESCRIPTION OF THE INVENTION

Figure 1A:
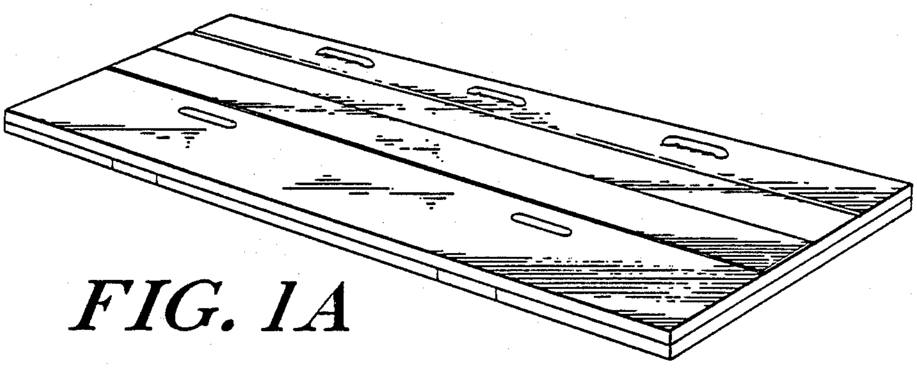
FIG. 1*a* shows a perspective view of the test tube rack in closed position.
Figure 1:
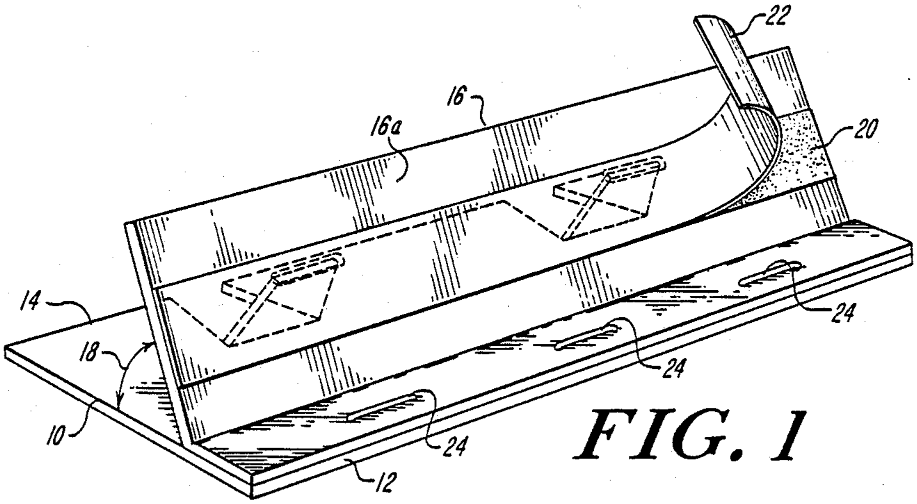
FIG. 1 shows a perspective see-through view of the test tube rack of the invention in assembled form.

Referring now to FIG. 1, there is shown a perspective see-through view of the disposable test tube rack of the invention. The rack has a base 10 with a forward edge 12 and a rear edge 14. Mounted on base 10 is a test tube-supporting member 16 having an outwardly-facing surface **16*a* and a rear surface (not numbered in the figure). As shown in the figure, test tube-supporting member 16 makes an angle 18 with base 10; angle 18 may be between 10° and 90° and is preferably between 75° and 85°. Located on the outwardly-facing surface 16*a* of test tube-supporting member 16 is at least one preferably horizontally mounted adhesive strip 20 which possesses an outwardly-facing layer of adhesive material. Adhesive layer 20 is covered by a protective strip 22 when the rack is not in use. Protective strip 22 is made of a material which does not adhere well to adhesive strip 20. Such protective strips are well known to the art and are typically made of waxed paper or plastic. Protective strip 22 is removed when the test tube rack is in use. Test tube-supporting member 16 is attached to base 10 by any convenient means, such as glue or staples 24** as shown in FIG. 1.

Figure 1B:
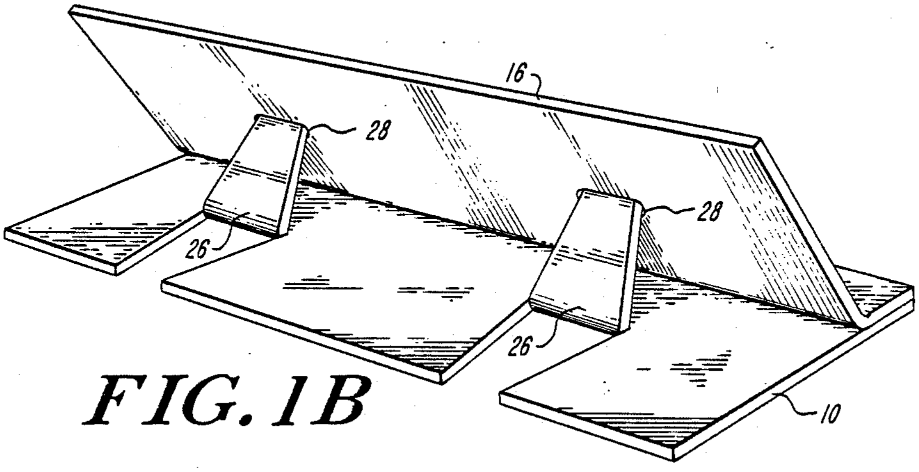
FIG. 1*b* shows a perspective view of the rear of the test tube rack.
Figure 2:
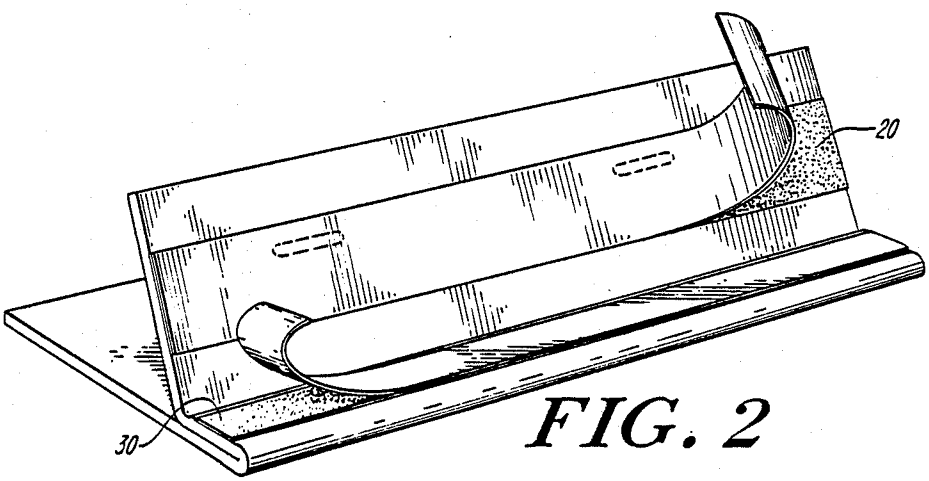
FIG. 2 shows an alternative embodiment of the test tube rack, in which an adhesive strip is located on the base.
Figure 3:
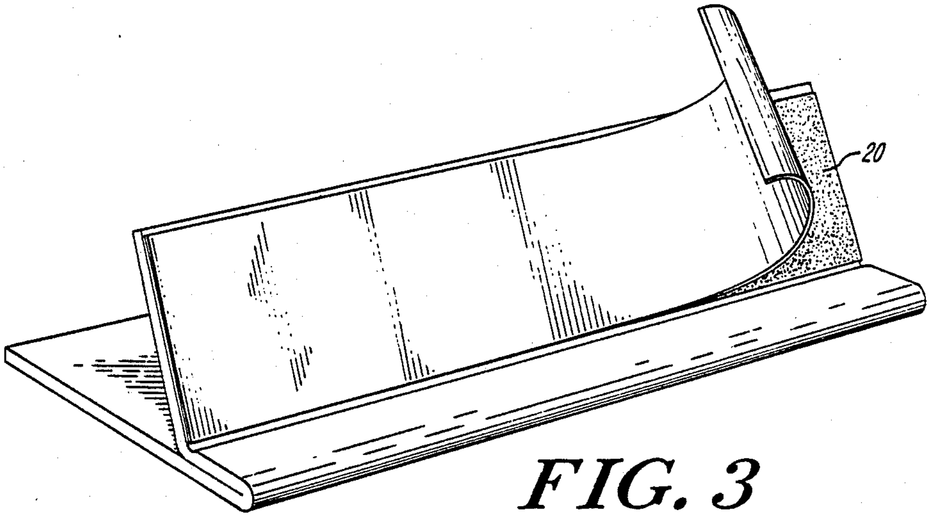
FIG. 3 shows an alternative embodiment of the test tube rack which employs a wide adhesive strip.

FIGS. 1 and 1*b* show that test tube-supporting member 16 is itself supported in position by orientable tabs 26 which are preferably cut from base 10. Tabs 26 fit into appropriately located slots 28 formed in test tube-supporting member 16. At least one such tab and slot combination is employed to support member 16, but two or more such combinations are preferably used. Test tube-supporting member 16 and base 10 may be formed from two separate pieces of material as shown in FIGS. 1, 1*a*, and 1*b*, or they may be part of a single piece of material, appropriately folded, as shown in FIGS. 2 and 3.

In the preferred embodiment, adhesive strip 20 has adhesive material on both sides, the adhesive on the outwardly-facing surface of the strip serving to hold test tubes, and the adhesive on the opposite surface serving to bond adhesive strip 20 to test tube-supporting member 16. Such a double sided tape may be used alone provided that outwardly-facing surface **16*a* of test tube-supporting member 16 bonds strongly to adhesive strip 20. In practice, however, double sided adhesive tapes capable of both holding and releasing test tubes may not bind strongly enough to test tube-supporting member 16. It is therefore preferred to employ a second double-sided tape between adhesive strip 20 and test tube-supporting member 16. This second tape is selected for its ability to bond tightly to both test tube-supporting member 16 and adhesive strip 20. This second tape is preferably placed over slots 28 in test tube-supporting member 16 so that when tabs 28 are inserted into these slots, they ae held there. Alternatively, a supplemental adhesive may be employed in slots 28 to hold tabs 26**.

The test tube rack is preferably made of cardboard, but may be constructed of other suitable materials such as plastic sheet, or other materials such as wood, fiberglass, metal, etc. which would suggest themselves to those skilled in the art.

The test tube rack possesses a number of advantages relative to previously known test tube racks. It is inexpensive, easily made in any desired size, and constructable from environmentally safe materials. Since it folds flat in the preferred embodiment and several of the alternative embodiments, it is easily stored, a large number fitting in a small space. It is very easily set up for use, and easily folded down for storage. It is simple to use—a test tube placed in contact with adhesive strip 20 is held positively on the rack until it is removed. It can hold many variously sized tubes at the same time because it has no holes or spaces into which the several sizes of tubes must fit. Since the test tubes are held at a single point against the test tube-supporting member 16, an unobstructed view of all the tubes is provided. It is easy to judge the colors of the test tube contents against the white background preferably employed for outwardly-facing test tube-supporting surface 16*a*, but where desirable for particular uses, the color of this surface may be changed readily. Since test tubes are held on the rack in a positive manner, the rack may be moved or manipulated with all the tubes attached, and may even be inverted to dump all the tubes at once. The test tube rack is sturdy, but if it is broken or damaged, it is readily repaired with such simple expedients as tape and staples. Finally, the unit is readily and safely disposable.

Figure 4:
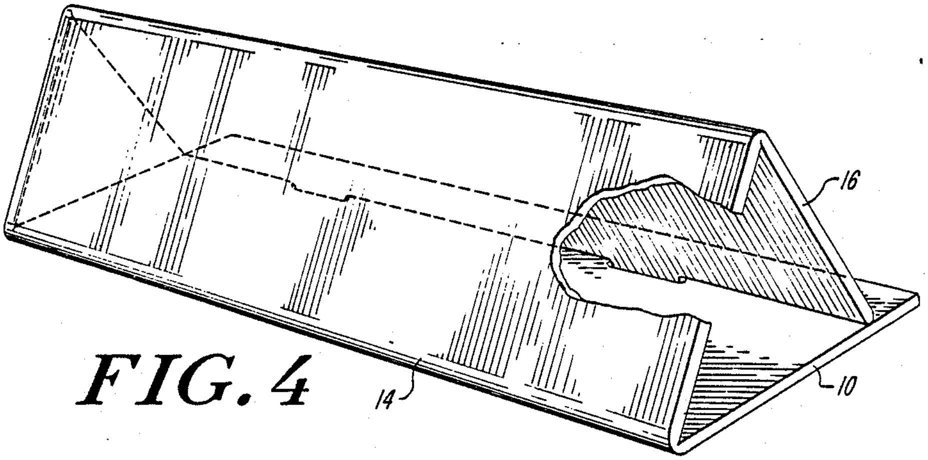
FIG. 4 shows an alternative embodiment of the test tube rack formed of a single flat piece of material shaped as a triangle.
Figure 6:
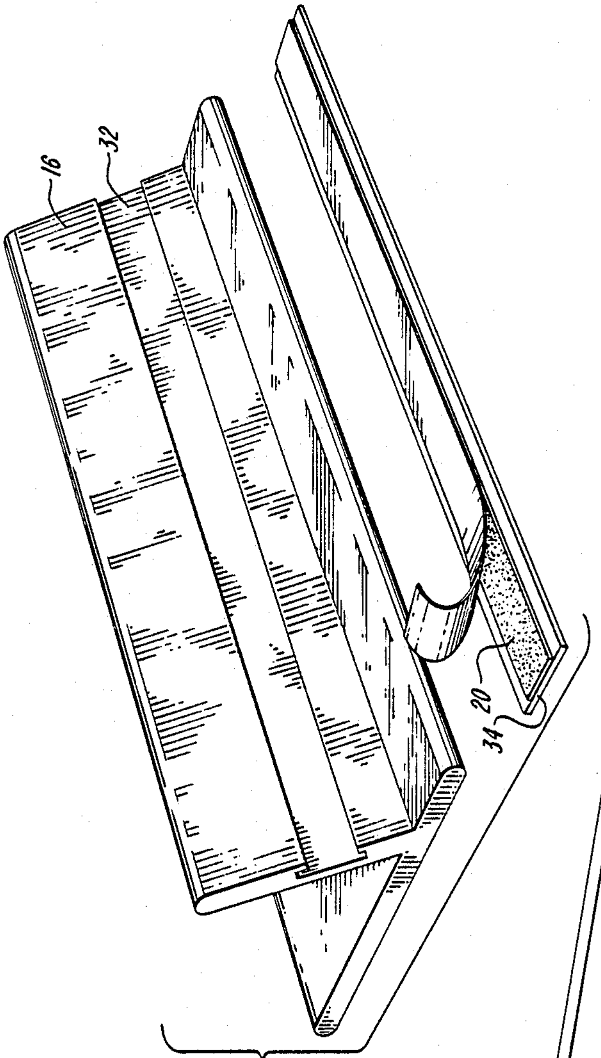
FIG. 6 shows an alternative embodiment of the test tube rack in which the adhesive strip is located on a replaceable insert which fits in a slot in the test tube-supporting member.
Figure 7:
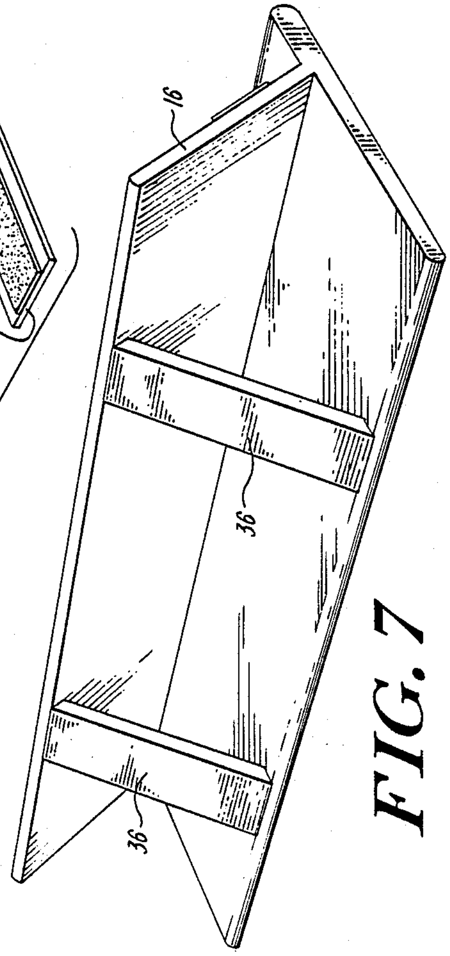
FIG. 7 shows an alternative embodiment of the test tube rack in which the test tube-supporting member is braced by separate buttressing members.
Figure 5:
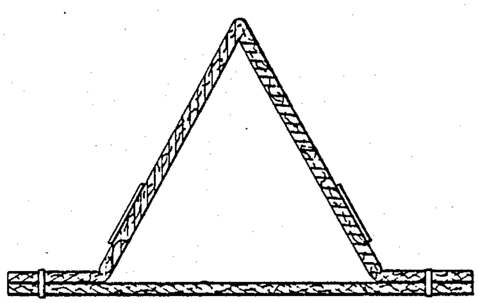
FIG. 5 is an alternative embodiment of the test tube rack in triangular form with two base extensions, for double sided use.
Figure 8:
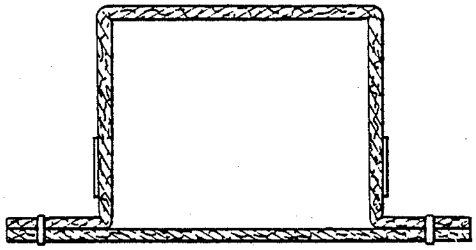
FIG. 8 is an alternative embodiment of the invention in the shape of a rectangle, for two-sided operation.
Figure 9:
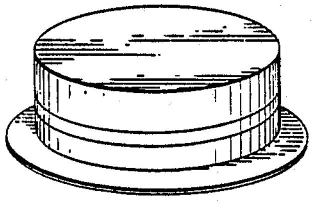
FIG. 9 is an alternative embodiment of the test tube rack, formed in a circular configuration.
Figure 10:
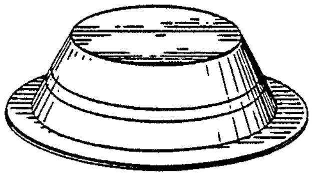
FIG. 10 is an alternative embodiment of the test tube rack, formed as a cone.
Figure 11:
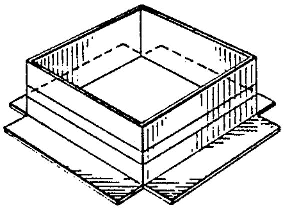
FIG. 11 is an alternative embodiment of the test tube rack, formed as a box for four-sided operation.

Many alternative embodiments of the test tube rack of the invention suggest themselves, some of these being shown in FIGS. 2–12. In FIG. 2, a base adhesive strip 30 is employed in addition to adhesive strip 20, to hold test tube bottoms firmly in place. In FIG. 3 adhesive strip 20 is wide, to provide a better grip in test tubes to be mounted on the rack. In FIG. 4, the test tube rack is formed of a single sheet of construction material folded into a triangular shape, the bottom of test tube-supporting member 16 being attached to base 10 via a slot and tab arrangement as shown in the figure, or by any other mechanism. In this embodiment, vertical support for test tube-supporting member 16 is provided by that section of the construction material connecting the base rear edge 14 with the top of test tube-supporting member 16. FIG. 5 shows a triangularly shaped two-sided version of the test tube rack, in which each of the test tube-supporting members supports the other. FIG. 6 shows that the test tube-supporting member 16 may be provided with a horizontal slot 32 adapted to receive and hold an appropriately shaped insert 34 carrying adhesive strip 20. In this embodiment, the test tube rack itself could be kept for a long time and the adhesive strips replaced as they became ineffective. In FIG. 7 it is shown that the test tube supporting member 16 may be buttressed by means of separate supporting braces 36. FIG. 8 shows a one-piece rack formed by bending a single sheet of construction material to form the base and the test tube-supporting member. FIG. 9 shows a two-sided embodiment in which the test tube-supporting members are vertically oriented relative to the base, and mutually supporting. FIGS. 10 and 11 show circular and conical embodiments respectively, in which test tubes may be mounted from any direction. FIG. 12 shows a four-sided box-type embodiment in which each of the test tube-supporting members is supported by the adjacent test tube-supporting members.

The invention has been described and exemplified in terms of particular embodiments, but it is to be recognized that other embodiments and other related modes of operation will suggest themselves to those skilled in the art, and that such additional alternatives are considered within the scope of the invention. Accordingly, the scope of this application is not to be limited except by the scope of the appended claims.

What is claimed is:

1. A collapsible test tube rack having open and closed conditions, said rack comprising:

a base having a front edge, a rear edge, and at least one orientable tab;

a test tube-supporting member having an outwardly-facing surface, a rear surface, and at least one slot, and having a length greater than its width, said member being pivotably connected along its length to said base along a line set back from the front edge of said base, said at least one slot and said at least one tab being mutually disposed such that in the open condition of said test tube rack said at least one tab connects with said at least one slot to prop said test tube-supporting member and in the closed condition of said test tube rack said at least one tab disconnects from said at least one slot and folds into said base, allowing said test tube-supporting member to fold down flat on said base; and at least one double-sided adhesive strip mounted on said outwardly-facing surface of said test tube-supporting member over said at least one slot, the side of said double-sided adhesive strip facing said test tube-supporting member serving to hold said strip on said test tube-supporting member and to hold said at least one tab in said at least one slot in the open condition of said test tube rack.

2. The test tube rack of claim 1 wherein said test tube-supporting member makes an angle with said base of between 10° and 90° in the open condition of said rack.

3. The test tube rack of claim 1 wherein said test tube-supporting member is provided with two slots and said base is provided with two orientable tabs.

4. The test tube rack of claim 1 further comprising:

a base adhesive strip on the upper surface of said base forward of said test tube-supporting member, said base adhesive strip having an upwardly-facing layer of adhesive material thereon.

5. The test tube rack of claim 1 wherein said at least one adhesive strip essentially covers said outwardly-facing surface of said test tube-supporting member.

* * * * *

UNITED STATES PATENT AND TRADEMARK OFFICE
CERTIFICATE OF CORRECTION

PATENT NO. : 4,748,125

DATED : May 31, 1988

INVENTOR(S) : John M. Pizzolante

It is certified that error appears in the above-identified patent and that said Letters Patent is hereby corrected as shown below:

Column 2, line 67, "ae" should read --are--.

Column 3, line 38, "grip in" should read --grip on--.

Signed and Sealed this

Thirty-first Day of July, 1990

*Attest:*

HARRY F. MANBECK, JR.

*Attesting Officer*

*Commissioner of Patents and Trademarks*